United States Patent [19]
Hermeling et al.

[11] Patent Number: 5,527,966
[45] Date of Patent: Jun. 18, 1996

[54] PREPARATION OF TRIPHENYLPHOSPHINE

[75] Inventors: Dieter Hermeling, Frankenthal; Peter Bassler, Viernheim; Peter Hammes, Ruppertsberg; Randolf Hugo, Mannheim; Peter Lechtken, Frankenthal; Hardo Siegel, Speyer, all of Germany

[73] Assignee: BASF Aktiengesellschaft, Ludwigshafen, Germany

[21] Appl. No.: 285,204

[22] Filed: Aug. 3, 1994

[30] Foreign Application Priority Data

Aug. 11, 1993 [DE] Germany .......................... 43 26 952.4

[51] Int. Cl.$^6$ ...................................... C07F 9/02
[52] U.S. Cl. ................................ 568/16; 568/17
[58] Field of Search ........................... 568/16, 17

[56] References Cited

U.S. PATENT DOCUMENTS 3,405,180  10/1968  Natoli ................................. 260/606.5
3,780,111  12/1973  Young et al. ..................... 260/606.5 P

FOREIGN PATENT DOCUMENTS 548682    6/1993  European Pat. Off. .
1192205   1/1966  Germany .
1029924   5/1966  United Kingdom .

Primary Examiner—Porfirio Nazario-Gonzales
Attorney, Agent, or Firm—Keil & Weinkauf

[57] ABSTRACT

Triphenylphosphine (TPP) is prepared by reacting triphenylphosphine dichloride (TPPCl$_2$) with magnesium, aluminum and/or iron in the presence of an inert solvent, employing a TPPCl$_2$ solution whose content of phosgene, chlorine, diphosgene, hydrogen chloride, thionyl chloride, sulfuryl chloride, phosphorus trichloride, phosphorus oxychloride and/or aliphatic halogen compounds (active chlorine compounds) totals less than 1000 ppm Cl.

9 Claims, 1 Drawing Sheet

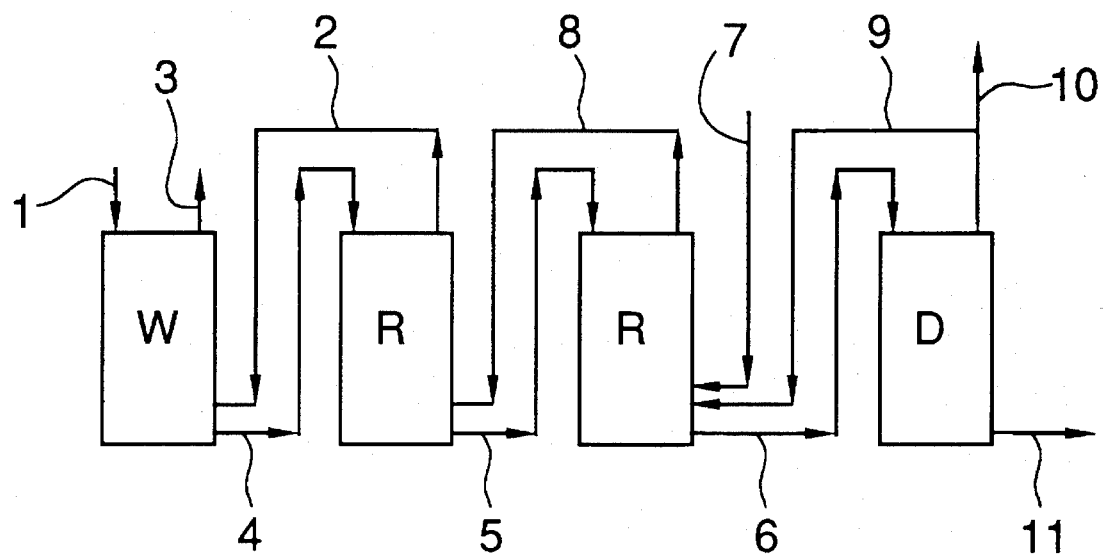

PREPARATION OF TRIPHENYLPHOSPHINE

The present invention relates to an improved process for preparing triphenylphosphine (TPP) by reacting triphenylphosphine dichloride (TPPCl$_2$) with magnesium, aluminum and/or iron in the presence of an inert solvent.

As is generally known, TPP is used on the industrial scale in the Wittig Ylide synthesis to prepare olefinic compounds such as vitamin A, the TPP being employed in the stoichiometric amount and being oxidized to triphenylphosphine oxide (TPPO).

Since only few uses of TPPO have been disclosed and since it is an extremely stable substance which can be disposed of only with difficulty, there have been numerous attempts to convert it back into TPP.

However, direct reduction using strong reducing agents such as alanates and silanes is too costly, and even the roundabout route via chlorination of TPPO with a chlorinating agent to give triphenylphosphine dichloride (TPPCl$_2$) and subsequent reduction of the TPPCl$_2$ with a less costly reducing agent is still economically unsatisfactory.

This also applies to the reaction sequence disclosed in DE-B 11 92 205 and GB-B 10 29 924 (page 2, lines 104 to 110)

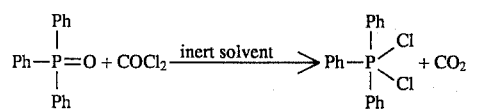

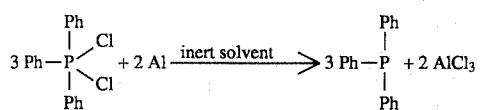

in which the starting materials are the low-cost phosgene and aluminum. Whereas almost complete conversion can be achieved on batchwise operation, a continuous procedure by combining the two reactions (1) and (2) proves to be extremely difficult. The reactions are relatively slow and thus only moderate yields of TPP are obtained using reactors of economic dimensions.

It is an object of the present invention to remedy this disadvantage and to make the conversion of TPPCl$_2$ into TPP more economic and mechanically simpler than hitherto.

We have found that this object is achieved by a process for preparing TPP by reacting TPPCl$_2$ with magnesium, aluminum and/or iron in the presence of an inert solvent, wherein a TPPCl$_2$ solution whose content of phosgene, chlorine, diphosgene, hydrogen chloride, thionyl chloride, sulfuryl chloride, phosphorus trichloride, phosphorus oxychloride and/or aliphatic halogen compounds (active chlorine compounds) totals less than 1000 ppm Cl is employed.

The invention also relates to the preparation of initial solutions which are composed of TPPCl$_2$ and the solvent and are suitable for this purpose, to the initial solutions themselves, and to a process for preparing TPPCl$_2$ by reacting TPPO with phosgene.

The chlorine content in this case is based on the total amount of said active chlorine compounds which are present from the outset in the TPPCl$_2$ solution or which may be produced in the preparation and in which the chlorine either is present in anionic form or can easily be converted into this form. The active chlorine compounds appear to favor the formation of chlorine-containing complex compounds of the reducing metal, and observations to date suggest that these seriously interfere with the progress of the reaction. Chlorine compounds in which the chlorine is firmly covalently bonded, for example aromatic chlorine compounds such as chlorobenzene or dichlorobenzene, are, by contrast, not a problem, for which reason they can be used as solvents. In general, the solvent should have an adequate dissolving power for the triphenylphosphorus compounds since, otherwise, the process can be operated only at relatively low concentrations and thus not economically. Preferred solvents are toluene and chlorobenzene.

The process according to the invention for preparing TPP is preferably carried out at about 60°–200° C., preferably from 80° to 175° C. The pressure in this process generally ranges from about 0.2 to 10 bar, and is preferably atmospheric.

The defined TPPCl$_2$ solution to be employed in the reduction stage is expediently obtained by heating the crude solution obtained from the reaction of TPPO with chlorinating agents such as thionyl chloride, phosphorus trichloride, phosphorus oxychloride or, preferably, phosgene to boiling, whereupon the active chlorine compounds are driven out of the solution together with part of the solvent in vapor form and preferably returned to the chlorination stage.

It is possible by means of this process to reduce the concentration of the active chlorine compounds in an economic and technically simple manner to less than 1000 ppm Cl in the solution. In a preferred embodiment, a distillation column is used for this purpose and may contain packings to increase the effectiveness. The boiling range of the process is about 100°–200° C., preferably 130°–175° C. Reduced pressure may be advisable to facilitate the removal of the active chlorine compounds.

A preferred embodiment for preparing the TPPCl$_2$ solutions according to the invention, whose content of phosgene, chlorine, diphosgene, hydrogen chloride, thionyl chloride, sulfuryl chloride, phosphorus trichloride, phosphorus oxychloride and/or aliphatic halogen compounds (active chlorine compounds) totals less than 1000 ppm Cl, comprises reacting triphenylphosphine oxide (TPPO) with phosgene in the inert solvent, wherein a) the TPPO-containing solution and the phosgene are passed countercurrently through one or more reaction vessels R arranged in series, b) the TPPO solution introduced into the system is enriched, in an upstream scrubber column W, with phosgene from the phosgene countercurrent under conditions such that the phosgene dissolves, and the CO$_2$ stream which may still contain some phosgene is removed from the scrubber column, and c) the solution which leaves the last of the reaction vessels R is transferred into a distillation column D from which the phosgene and the active chlorine compounds are removed together with part of the solvent by distillation, this mixture being returned to the last reaction vessel in which the fresh phosgene is also introduced countercurrently to the solution, and the TPPCl$_2$ solution being removed from the bottom part of D.

BRIEF DESCRIPTION OF THE DRAWING

The drawing is a schematic representation of a system designed to continuously produce TPPCl$_2$ solutions.

This process is described in detail hereinafter with the aid of the drawing. The TPPO-containing solution and the phosgene are passed in countercurrent through one or more reaction vessels R arranged in series. This results in chlorination of TPPO to TPPCl$_2$ in accordance with equation (1). The reaction preferably takes place at about 60°–150° C., particularly preferably 80°–130° C., and expediently under atmospheric pressure. Higher pressures, up to about 10 bar, may be advisable in the case of low-boiling solvents.

In place of a plurality of reaction vessels, eg. stirred vessels, which are arranged in series and which can be operated with increasing temperature, it is also possible to use a single reaction vessel, preferably a reaction column. Preferred reaction columns for economic reasons are packed columns, but columns of any design are suitable in principle, eg. bubble cap and perforated plate columns.

The TPPO solution introduced into the system through line (1) is, before being fed into the first reaction vessel (R), passed countercurrently in a upstream scrubber column (W) to the gas stream from the first reaction vessel, which reaches the scrubber column (W) through line (2). The conditions in the scrubber column are adjusted so that a large proportion of the phosgene from the gas stream dissolves. The temperature in the scrubber column under atmospheric pressure is about 0°–100° C. preferably 20°–60° C. Altering the pressure has an effect on the dissolving behavior. The solubility of phosgene is increased by raising the pressure up to about 5 bar. The gas stream removed from the scrubber column through line (3) is mainly composed of $CO_2$ and now contains little phosgene. The solution enriched with phosgene is fed via line (4) to the first reaction vessel. The solution is removed from the first reaction vessel and passed into a second reaction vessel through line (5). Fresh phosgene is introduced into the last reaction vessel through line (7). The gas stream removed from this reaction vessel is passed through line (8) countercurrently to the solution into the upstream reaction vessel.

The solution leaving the last of the reaction vessels R is introduced through line (6) into a distillation column (D) which may contain commercial internals to increase the effectiveness. Suitable examples are bubble cap and packed columns. The distillation column is operated in the same way as for preparing the $TPPCl_2$ solution whose concentration of active chlorine compounds is less than 1000 ppm Cl. The vapors which contain the chlorine compounds are, where appropriate after condensation, returned through line (9) into the last of the reaction vessels R. To prevent the chlorine compounds accumulating over the course of time in the apparatus system comprising W, R and D, it is advisable for part of the vapors which leave D to be extracted through line (10) and worked up to pure solvent, and for the solvent then to be returned to the system. The lines between the apparatuses, especially between W and R, can be equipped with heat exchangers, and transport of materials can be carried out with conveying units such as pumps or compressors. All apparatus parts which come into contact with the aggressive reaction mixture ought expediently to be made of corrosion-resistant material.

Besides the preferred countercurrent procedure, the TPPO solution and the phosgene can also be passed cocurrently to the reaction vessels, in which case the same applies analogously as for the countercurrent process.

The $TPPCl_2$ solution which leaves D through line (11) can be fed directly to the reaction with the reducing metal, preferably aluminum, under conventional conditions. The metal is preferably employed in the form of powder, and the reaction is carried out at 60°–200° C., preferably 80°–175° C.

In an expedient embodiment of the process according to the invention, the conversion of TPPO to $TPPCl_2$ takes place in the presence of a phosgenation catalyst such as, preferably, an N,N-disubstituted formamide. These compounds react with phosgene to form Vilsmeyer compounds which actually carry out the chlorination with liberation of the formamides again. Since the formamides are liberated again they are effective even in small amounts. Particularly suitable are N,N-dialkylformamides with a total of up to 12 carbon atoms in the alkyl radicals, and these alkyl radicals can also be linked to form a 5- to 7-membered ring.

After the reaction is complete, water is added to the mixture, resulting in an aqueous phase containing the metal salt and hydrochloric acid.

The organic phase is expediently worked up by distillation to give pure TPP in a yield of about 95% based on TPPO. Without the reduction, according to the invention, in the concentration of active chlorine compounds, the yield of pure TPP is only about 85–90%.

EXAMPLE

Preparation of Triphenylphosphine

About 880 g/h of a solution of triphenylphosphine oxide (TPPO) and chlorobenzene, the TPPO content being 12.5% by weight, were metered into a scrubber column with a height of 22 cm and a diameter of 3 cm. The scrubber column contained 3 mm diameter glass packings and was operated at about 50° C.

The subsequent chlorination was carried out in two stirred vessels, each with a capacity of one liter, arranged in series. The stirrer speed was 400 rpm in each of these, and the temperature was about 100° C. The countercurrent phosgene stream amounted to 43.6 g/h.

The downstream distillation column comprised a bubble cap column with a height of 55 cm and a diameter of 3 cm. This bubble cap column contained 11 plates and was operated at about 135° C.

The product obtained from the distillation column was subsequently reduced with aluminum powder with an average particle diameter of about 200–400 μm at about 130° C.

The experiment lasted 211 hours. In total, 23,210 g of TPPO, 9200 g of phosgene and 1519 g of aluminum were employed. The yield of triphenylphosphine was 96%.

Comparative Experiment

The comparative experiment was carried out under the abovementioned conditions but without using a distillation column to reduce the content of active chlorine compounds. The discharge from the stirred vessels was subjected directly to aluminum reduction.

The TPPO and phosgene mass streams were the same as in the first experiment, and the TPPO content in the chlorobenzene was likewise 12.5% by weight. 7.5 g/h of aluminum were required for the subsequent reduction.

In total, 43,340 g of TPPO, 17,178 g of phosgene and 2955 g of aluminum were employed. The yield of triphenylphosphine was about 87%.

We claim:

1. In a process for preparing triphenylphosphine (TPP) by reacting triphenylphosphine dichloride ($TPPCl_2$) with magnesium, aluminum and/or iron in the presence of an inert solvent, the improvement which comprises: employing in the reaction a $TPPCl_2$ solution whose content of phosgene, chlorine, diphosgene, hydrogen chloride, thionyl chloride, sulfuryl chloride, phosphorus trichloride, phosphorus oxychloride and/or aliphatic halogen compounds (active chlorine compounds) totals less than 1000 ppm Cl.

2. A process as defined in claim 1, wherein the TPPCl$_2$ is reacted with aluminum.

3. An improved process as defined in claim 1, wherein the solution which is composed of TPPCl$_2$ and an inert solvent and whose content of phosgene, chloride, diphosgene, hydrogen chloride, thionyl chloride, sulfuryl chloride, phosphorus trichloride, phosphorus oxychloride and/or aliphatic halogen compounds (active chlorine compounds) totals less than 1000 ppm Cl, is prepared by subjecting an initial solution in which the chlorine concentration is above 1000 ppm to distillation to remove chlorine together with part of the solvent.

4. A process for the continuous preparation of solutions which are composed of an inert solvent and TPPCl$_2$ and whose content of phosgene, chloride, diphosgene, hydrogen chloride, thionyl chloride, sulfuryl chloride, phosphorus trichloride, phosphorus oxychloride and/or aliphatic halogen compounds (active chlorine compounds) is less than 1000 ppm Cl by reacting triphenylphosphine oxide (TPPO) with phosgene in the inert solvent, wherein a) the TPPO-containing solution and the phosgene are passed countercurrently through one or more reaction vessels R arranged in series, b) the TPPO solution introduced into the system is enriched, in an upstream scrubber column W, with phosgene from the phosgene countercurrent under conditions such that the phosgene dissolves, and the CO$_2$ stream which may still contain some phosgene is removed from the scrubber column, and c) the solution which leaves the last of the reaction vessels R is transferred into a distillation column D from which the phosgene and the active chlorine compounds are removed together with part of the solvent by distillation, this mixture being returned to the last reaction vessel in which the fresh phosgene is also introduced countercurrently to the solution, and the TPPCl$_2$ solution being removed from the bottom part of D.

5. A modification of the process as claimed in claim 4, wherein the TPPO and the phosgene flow cocurrently through the apparatuses R.

6. A process as claimed in claim 4, wherein the reaction of TPPO with phosgene is carried out in the presence of a phosgenation catalyst.

7. A process as claimed in claim 5, wherein the reaction of TPPO with phosgene is carried out in the presence of a phosgenation catalyst.

8. A process as claimed in claim 6, wherein an N,N-disubstituted formamide is used as phosgenation catalyst.

9. A process as claimed in claim 7, wherein an N,N-disubstituted formamide is used as phosgenation catalyst.

* * * * *